US011554214B2

(12) United States Patent
Toth (10) Patent No.: US 11,554,214 B2
(45) Date of Patent: Jan. 17, 2023

(54) FLUID MANAGEMENT SYSTEM (71) Applicant: Meditrina, Inc., Cupertino, CA (US)

(72) Inventor: Akos Toth, Cupertino, CA (US)

(73) Assignee: Meditrina, Inc., Cupertino, CA (US)

( * ) Notice: Subject to any disclaimer, the term of this patent is extended or adjusted under 35 U.S.C. 154(b) by 81 days.

(21) Appl. No.: 16/909,599

(22) Filed: Jun. 23, 2020

(65) Prior Publication Data

US 2020/0405953 A1 Dec. 31, 2020

Related U.S. Application Data (60) Provisional application No. 62/866,876, filed on Jun. 26, 2019.

(51) Int. Cl.
*A61M 5/168* (2006.01)
*A61M 5/142* (2006.01)

(52) U.S. Cl.
CPC .......... *A61M 5/1684* (2013.01); *A61M 5/142* (2013.01); *A61M 5/14232* (2013.01); *A61M 5/16804* (2013.01); *A61M 5/16854* (2013.01); *A61M 5/16886* (2013.01); *A61M 2005/14208* (2013.01); *A61M 2205/18* (2013.01);
(Continued)

(58) Field of Classification Search
CPC ............ A61M 5/1684; A61M 5/14228; A61M 5/14232
See application file for complete search history.

(56) References Cited

U.S. PATENT DOCUMENTS 3,903,891 A 9/1975 Brayshaw
4,428,748 A 1/1984 Peyman et al.
(Continued)

FOREIGN PATENT DOCUMENTS

CN 1977194 A 6/2007
CN 101015474 A 8/2007
(Continued)

OTHER PUBLICATIONS

Notice of Allowance dated Oct. 19, 2020 for U.S. Appl. No. 14/657,684.
(Continued)

*Primary Examiner* — Jenna Zhang
(74) *Attorney, Agent, or Firm* — Wilson Sonsini Goodrich & Rosati (57) ABSTRACT

A surgical fluid management system includes a console and a cassette for delivering fluids to a surgical site. The console has a pump rotor and a pressure-sensing membrane. The cassette has a cassette housing, a flexible fluid delivery tube in the housing. The flexible fluid delivery tube has a lumen configured to interface with the pump rotor and to deliver a flow of fluid from a fluid source as the rotor is rotated. A pressure-transmitting membrane is located in a wall of the cassette housing and in fluid communication with said fluid delivery lumen. The pressure-transmitting membrane flexes outwardly in response to a positive pressure in the lumen and flexes inwardly in response to a negative pressure in the lumen. The pressure-transmitting membrane detachably adheres to or presses against the pressure-sensing membrane to cause the pressure-sensing membrane to move in response to pressure changes in the flexible fluid delivery tube.

6 Claims, 6 Drawing Sheets (52) U.S. Cl.
CPC ............... *A61M 2205/3334* (2013.01); *A61M 2205/3389* (2013.01)

(56) References Cited

U.S. PATENT DOCUMENTS

| | | | |
|---|---|---|---|
| 4,949,718 A | 8/1990 | Neuwirth et al. |
| 4,979,948 A | 12/1990 | Geddes et al. |
| 4,989,583 A | 2/1991 | Hood |
| 5,045,056 A | 9/1991 | Behl |
| 5,078,717 A | 1/1992 | Parins et al. |
| 5,084,044 A | 1/1992 | Quint |
| 5,085,659 A | 2/1992 | Rydell et al. |
| 5,191,883 A | 3/1993 | Lennox et al. |
| 5,197,963 A | 3/1993 | Parins |
| 5,242,390 A | 9/1993 | Goldrath |
| 5,248,312 A | 9/1993 | Langberg |
| 5,269,794 A | 12/1993 | Rexroth |
| 5,277,201 A | 1/1994 | Stern et al. |
| 5,282,799 A | 2/1994 | Rydell |
| 5,324,254 A | 6/1994 | Phillips |
| 5,344,435 A | 9/1994 | Turner et al. |
| 5,374,261 A | 12/1994 | Yoon |
| 5,401,272 A | 3/1995 | Perkins |
| 5,401,274 A | 3/1995 | Kusunoki |
| 5,429,136 A | 7/1995 | Milo et al. |
| 5,441,498 A | 8/1995 | Perkins |
| 5,443,470 A | 8/1995 | Stern et al. |
| 5,456,689 A | 10/1995 | Kresch et al. |
| 5,483,994 A | 1/1996 | Maurer |
| 5,496,314 A | 3/1996 | Eggers |
| 5,501,681 A | 3/1996 | Neuwirth et al. |
| 5,505,730 A | 4/1996 | Edwards |
| 5,507,725 A | 4/1996 | Savage et al. |
| 5,558,672 A | 9/1996 | Edwards et al. |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | Lafontaine et al. |
| 5,592,727 A | 1/1997 | Glowa et al. |
| 5,622,647 A | 4/1997 | Kerr et al. |
| 5,647,848 A | 7/1997 | Jorgensen |
| 5,653,684 A | 8/1997 | Laptewicz et al. |
| 5,653,692 A | 8/1997 | Masterson et al. |
| 5,662,647 A | 9/1997 | Crow et al. |
| 5,672,174 A | 9/1997 | Gough et al. |
| 5,681,308 A | 10/1997 | Edwards et al. |
| 5,697,281 A | 12/1997 | Eggers et al. |
| 5,697,882 A | 12/1997 | Eggers et al. |
| 5,713,942 A | 2/1998 | Stern et al. |
| 5,733,298 A | 3/1998 | Berman et al. |
| 5,769,846 A | 6/1998 | Edwards et al. |
| 5,769,880 A | 6/1998 | Truckai et al. |
| 5,779,662 A | 7/1998 | Berman |
| 5,800,493 A | 9/1998 | Stevens et al. |
| 5,810,802 A | 9/1998 | Panescu et al. |
| 5,827,273 A | 10/1998 | Edwards |
| 5,833,644 A | 11/1998 | Zadno-Azizi et al. |
| 5,843,020 A | 12/1998 | Tu et al. |
| 5,846,239 A | 12/1998 | Swanson et al. |
| 5,860,974 A | 1/1999 | Abele et al. |
| 5,866,082 A | 2/1999 | Hatton et al. |
| 5,876,340 A | 3/1999 | Tu et al. |
| 5,879,347 A | 3/1999 | Saadat et al. |
| 5,891,094 A | 4/1999 | Masterson et al. |
| 5,891,134 A | 4/1999 | Goble et al. |
| 5,891,136 A | 4/1999 | McGee et al. |
| 5,902,251 A | 5/1999 | Vanhooydonk |
| 5,904,651 A | 5/1999 | Swanson et al. |
| 5,925,038 A | 7/1999 | Panescu et al. |
| 5,954,714 A | 9/1999 | Saadat et al. |
| 5,958,782 A | 9/1999 | Bentsen et al. |
| 5,964,755 A | 10/1999 | Edwards |
| 5,976,129 A | 11/1999 | Desai |
| 5,980,515 A | 11/1999 | Tu |
| 5,997,534 A | 12/1999 | Tu et al. |
| 6,024,743 A | 2/2000 | Edwards |
| 6,026,331 A | 2/2000 | Feldberg et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,091,993 A | 7/2000 | Bouchier et al. |
| 6,113,597 A | 9/2000 | Eggers et al. |
| 6,136,014 A | 10/2000 | Sirimanne et al. |
| 6,139,570 A | 10/2000 | Saadat et al. |
| 6,146,378 A | 11/2000 | Mikus et al. |
| 6,149,620 A | 11/2000 | Baker et al. |
| 6,214,003 B1 | 4/2001 | Morgan et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallsten et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon et al. |
| 6,409,722 B1 | 6/2002 | Hoey et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,491,690 B1 | 12/2002 | Goble et al. |
| 6,508,815 B1 | 1/2003 | Strul et al. |
| 6,551,310 B1 | 4/2003 | Ganz et al. |
| 6,565,561 B1 | 5/2003 | Goble et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,622,731 B2 | 9/2003 | Daniel et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | Vandusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,905,497 B2 | 6/2005 | Truckai et al. |
| 6,923,805 B1 | 8/2005 | Lafontaine et al. |
| 6,929,642 B2 | 8/2005 | Xiao et al. |
| 6,949,096 B2 | 9/2005 | Davison et al. |
| 6,951,569 B2 | 10/2005 | Nohilly et al. |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fjield et al. |
| 7,087,052 B2 | 8/2006 | Sampson et al. |
| 7,108,696 B2 | 9/2006 | Daniel et al. |
| 7,118,590 B1 | 10/2006 | Cronin |
| 7,150,747 B1 | 12/2006 | McDonald et al. |
| 7,175,734 B2 | 2/2007 | Stewart et al. |
| 7,179,255 B2 | 2/2007 | Lettice et al. |
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,278,994 B2 | 10/2007 | Goble et al. |
| 7,294,126 B2 | 11/2007 | Sampson et al. |
| 7,297,143 B2 | 11/2007 | Woloszko et al. |
| 7,326,201 B2 | 2/2008 | Fjield et al. |
| 7,331,957 B2 | 2/2008 | Woloszko et al. |
| RE40,156 E | 3/2008 | Sharps et al. |

(56) References Cited

U.S. PATENT DOCUMENTS

| | | |
|---|---|---|
| 7,371,231 B2 | 5/2008 | Rioux et al. |
| 7,371,235 B2 | 5/2008 | Thompson et al. |
| 7,381,208 B2 | 6/2008 | Van et al. |
| 7,387,628 B1 | 6/2008 | Behl et al. |
| 7,390,330 B2 | 6/2008 | Harp |
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,744,595 B2 | 6/2010 | Truckai et al. |
| 7,749,159 B2 | 7/2010 | Crowley et al. |
| 7,824,398 B2 | 11/2010 | Woloszko et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 | 7/2011 | Felts et al. |
| 8,012,153 B2 | 9/2011 | Woloszko et al. |
| 8,016,843 B2 | 9/2011 | Escaf |
| 8,197,476 B2 | 6/2012 | Truckai |
| 8,197,477 B2 | 6/2012 | Truckai |
| 8,323,280 B2 | 12/2012 | Germain et al. |
| 8,372,068 B2 | 2/2013 | Truckai |
| 8,382,753 B2 | 2/2013 | Truckai |
| 8,486,096 B2 | 7/2013 | Robertson et al. |
| 8,500,732 B2 | 8/2013 | Truckai et al. |
| 8,540,708 B2 | 9/2013 | Truckai et al. |
| 8,657,174 B2 | 2/2014 | Yates et al. |
| 8,690,873 B2 | 4/2014 | Truckai et al. |
| 8,728,003 B2 | 5/2014 | Taylor et al. |
| 8,821,486 B2 | 9/2014 | Toth et al. |
| 8,998,901 B2 | 4/2015 | Truckai et al. |
| 9,204,918 B2 | 12/2015 | Germain et al. |
| 9,277,954 B2 | 3/2016 | Germain et al. |
| 9,427,249 B2 | 8/2016 | Robertson et al. |
| 9,472,382 B2 | 10/2016 | Jacofsky |
| 9,510,850 B2 | 12/2016 | Robertson et al. |
| 9,510,897 B2 | 12/2016 | Truckai |
| 9,585,675 B1 | 3/2017 | Germain et al. |
| 9,592,085 B2 | 3/2017 | Germain et al. |
| 9,603,656 B1 | 3/2017 | Germain et al. |
| 9,649,125 B2 | 5/2017 | Truckai |
| 9,651,423 B1 | 5/2017 | Zhang |
| 9,662,163 B2 | 5/2017 | Toth et al. |
| 9,855,675 B1 | 1/2018 | Germain et al. |
| 9,901,394 B2 | 2/2018 | Shadduck et al. |
| 9,999,466 B2 | 6/2018 | Germain et al. |
| 10,004,556 B2 | 6/2018 | Orczy-Timko et al. |
| 10,052,149 B2 | 8/2018 | Germain et al. |
| 10,213,246 B2 | 2/2019 | Toth et al. |
| 10,492,856 B2 | 12/2019 | Orczy-Timko |
| 10,517,578 B2 | 12/2019 | Truckai |
| 10,595,889 B2 | 3/2020 | Germain et al. |
| 10,617,461 B2 | 4/2020 | Toth et al. |
| 10,662,939 B2 | 5/2020 | Orczy-Timko et al. |
| 10,912,606 B2 | 2/2021 | Truckai et al. |
| 11,259,787 B2 | 3/2022 | Truckai |
| 2001/0004444 A1 | 6/2001 | Haser et al. |
| 2002/0058933 A1 | 5/2002 | Christopherson et al. |
| 2002/0062142 A1 | 5/2002 | Knowlton |
| 2002/0068934 A1 | 6/2002 | Edwards et al. |
| 2002/0082635 A1 | 6/2002 | Kammerer et al. |
| 2002/0183742 A1 | 12/2002 | Carmel et al. |
| 2003/0060813 A1 | 3/2003 | Loeb et al. |
| 2003/0065321 A1 | 4/2003 | Carmel et al. |
| 2003/0153905 A1 | 8/2003 | Edwards et al. |
| 2003/0153908 A1 | 8/2003 | Goble et al. |
| 2003/0171743 A1 | 9/2003 | Tasto et al. |
| 2003/0176816 A1 | 9/2003 | Maguire et al. |
| 2003/0216725 A1 | 11/2003 | Woloszko et al. |
| 2003/0236487 A1 | 12/2003 | Knowlton et al. |
| 2004/0002702 A1 | 1/2004 | Xiao et al. |
| 2004/0010249 A1 | 1/2004 | Truckai et al. |
| 2004/0087936 A1 | 5/2004 | Stern et al. |
| 2004/0092980 A1 | 5/2004 | Cesarini et al. |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0075630 A1 | 4/2005 | Truckai et al. |
| 2005/0145009 A1* | 7/2005 | Vanderveen ...... A61M 5/16854 73/1.57 |
| 2005/0165389 A1 | 7/2005 | Swain et al. |
| 2005/0182397 A1 | 8/2005 | Ryan |
| 2005/0187546 A1 | 8/2005 | Bek et al. |
| 2005/0192652 A1 | 9/2005 | Cioanta et al. |
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0084158 A1 | 4/2006 | Viol |
| 2006/0084969 A1 | 4/2006 | Truckai et al. |
| 2006/0089637 A1 | 4/2006 | Werneth et al. |
| 2006/0189971 A1 | 8/2006 | Tasto et al. |
| 2006/0189976 A1 | 8/2006 | Karni et al. |
| 2006/0200040 A1 | 9/2006 | Weikel, Jr. et al. |
| 2006/0224154 A1 | 10/2006 | Shadduck et al. |
| 2006/0259025 A1 | 11/2006 | Dahla |
| 2007/0021743 A1 | 1/2007 | Rioux et al. |
| 2007/0027447 A1 | 2/2007 | Theroux et al. |
| 2007/0083192 A1 | 4/2007 | Welch |
| 2007/0161981 A1 | 7/2007 | Sanders et al. |
| 2007/0213704 A1 | 9/2007 | Truckai et al. |
| 2007/0276430 A1 | 11/2007 | Lee et al. |
| 2007/0282323 A1 | 12/2007 | Woloszko et al. |
| 2007/0287996 A1 | 12/2007 | Rioux |
| 2007/0288075 A1 | 12/2007 | Dowlatshahi |
| 2007/0293853 A1 | 12/2007 | Truckai et al. |
| 2008/0045859 A1 | 2/2008 | Fritsch et al. |
| 2008/0058797 A1 | 3/2008 | Rioux |
| 2008/0091061 A1 | 4/2008 | Kumar et al. |
| 2008/0097242 A1 | 4/2008 | Cai |
| 2008/0097425 A1 | 4/2008 | Truckai |
| 2008/0125765 A1 | 5/2008 | Berenshteyn et al. |
| 2008/0125770 A1 | 5/2008 | Kleyman |
| 2008/0154238 A1 | 6/2008 | McGuckin |
| 2008/0183132 A1 | 7/2008 | Davies et al. |
| 2008/0208189 A1 | 8/2008 | Van et al. |
| 2008/0221567 A1 | 9/2008 | Sixto et al. |
| 2008/0249518 A1 | 10/2008 | Warnking et al. |
| 2008/0249533 A1 | 10/2008 | Godin |
| 2008/0281317 A1 | 11/2008 | Gobel et al. |
| 2009/0048593 A1 | 2/2009 | Ganz et al. |
| 2009/0054888 A1 | 2/2009 | Cronin |
| 2009/0054892 A1 | 2/2009 | Rioux et al. |
| 2009/0076494 A1 | 3/2009 | Azure |
| 2009/0105703 A1 | 4/2009 | Shadduck |
| 2009/0131927 A1 | 5/2009 | Kastelein et al. |
| 2009/0149846 A1 | 6/2009 | Hoey et al. |
| 2009/0163908 A1 | 6/2009 | MacLean et al. |
| 2009/0209956 A1 | 8/2009 | Marion |
| 2009/0234348 A1 | 9/2009 | Bruszewski et al. |
| 2009/0259150 A1 | 10/2009 | Ostrovsky et al. |
| 2009/0270899 A1 | 10/2009 | Carusillo et al. |
| 2009/0306654 A1 | 12/2009 | Garbagnati |
| 2010/0004595 A1 | 1/2010 | Nguyen et al. |
| 2010/0036372 A1 | 2/2010 | Truckai et al. |
| 2010/0036488 A1 | 2/2010 | De, Jr. et al. |
| 2010/0042095 A1 | 2/2010 | Bigley et al. |
| 2010/0042097 A1 | 2/2010 | Newton et al. |

(56) References Cited

U.S. PATENT DOCUMENTS

| | | |
|---|---|---|
| 2010/0049190 A1 | 2/2010 | Long et al. |
| 2010/0094289 A1 | 4/2010 | Taylor et al. |
| 2010/0121319 A1 | 5/2010 | Chu et al. |
| 2010/0125269 A1 | 5/2010 | Emmons et al. |
| 2010/0137855 A1 | 6/2010 | Berjano et al. |
| 2010/0137857 A1 | 6/2010 | Shroff et al. |
| 2010/0152725 A1 | 6/2010 | Pearson et al. |
| 2010/0185191 A1 | 7/2010 | Carr et al. |
| 2010/0198214 A1 | 8/2010 | Layton, Jr. et al. |
| 2010/0204688 A1 | 8/2010 | Hoey et al. |
| 2010/0217245 A1 | 8/2010 | Prescott |
| 2010/0217256 A1 | 8/2010 | Strul et al. |
| 2010/0228239 A1 | 9/2010 | Freed |
| 2010/0228245 A1 | 9/2010 | Sampson et al. |
| 2010/0234867 A1 | 9/2010 | Himes |
| 2010/0286680 A1 | 11/2010 | Kleyman |
| 2010/0286688 A1 | 11/2010 | Hughett, Sr. et al. |
| 2011/0004205 A1 | 1/2011 | Chu et al. |
| 2011/0046513 A1 | 2/2011 | Hibner |
| 2011/0060391 A1 | 3/2011 | Unetich et al. |
| 2011/0112524 A1 | 5/2011 | Stern et al. |
| 2011/0196401 A1 | 8/2011 | Robertson et al. |
| 2011/0196403 A1 | 8/2011 | Robertson et al. |
| 2011/0282340 A1 | 11/2011 | Toth et al. |
| 2011/0306968 A1 | 12/2011 | Beckman et al. |
| 2012/0041434 A1 | 2/2012 | Truckai |
| 2012/0330292 A1 | 12/2012 | Shadduck et al. |
| 2013/0090642 A1 | 4/2013 | Shadduck et al. |
| 2013/0103021 A1 | 4/2013 | Germain et al. |
| 2013/0172870 A1 | 7/2013 | Germain et al. |
| 2013/0231652 A1 | 9/2013 | Germain et al. |
| 2013/0237780 A1 | 9/2013 | Beasley et al. |
| 2013/0267937 A1 | 10/2013 | Shadduck et al. |
| 2013/0289558 A1 | 10/2013 | Reid, Jr. et al. |
| 2013/0296847 A1 | 11/2013 | Germain et al. |
| 2013/0331833 A1 | 12/2013 | Bloom |
| 2014/0336632 A1 | 11/2014 | Toth et al. |
| 2014/0336643 A1 | 11/2014 | Orczy-Timko et al. |
| 2014/0358077 A1* | 12/2014 | Oruklu ............... A61M 5/1684 604/111 |
| 2015/0119795 A1 | 4/2015 | Germain et al. |
| 2015/0119916 A1 | 4/2015 | Dietz et al. |
| 2015/0173827 A1 | 6/2015 | Bloom et al. |
| 2015/0182281 A1 | 7/2015 | Truckai et al. |
| 2016/0066982 A1 | 3/2016 | Marczyk et al. |
| 2016/0095615 A1 | 4/2016 | Orczy-Timko et al. |
| 2016/0113706 A1 | 4/2016 | Truckai et al. |
| 2016/0120443 A1* | 5/2016 | Margalit ............... A61B 5/1073 600/587 |
| 2016/0157916 A1 | 6/2016 | Germain et al. |
| 2016/0287779 A1* | 10/2016 | Orczy-Timko ..... A61M 3/0201 |
| 2016/0346036 A1 | 12/2016 | Orczy-Timko et al. |
| 2017/0231681 A1 | 8/2017 | Toth et al. |
| 2017/0258519 A1 | 9/2017 | Germain et al. |
| 2017/0303990 A1 | 10/2017 | Benamou et al. |
| 2017/0348493 A1 | 12/2017 | Wells et al. |
| 2018/0001009 A1 | 1/2018 | Crawford et al. |
| 2018/0010599 A1* | 1/2018 | Hernandez Martinez .................. B41F 33/00 |
| 2018/0147003 A1 | 5/2018 | Shadduck et al. |
| 2018/0326144 A1 | 11/2018 | Truckai |
| 2018/0369477 A1 | 12/2018 | Ding et al. |
| 2019/0030235 A1 | 1/2019 | Orczy-Timko et al. |
| 2019/0192218 A1 | 6/2019 | Orczy-Timko et al. |
| 2020/0030527 A1 | 1/2020 | Toth et al. |
| 2020/0222104 A1 | 7/2020 | Toth et al. |
| 2020/0330085 A1 | 10/2020 | Truckai |
| 2021/0038279 A1 | 2/2021 | Toth et al. |
| 2021/0346087 A1 | 11/2021 | Truckai et al. |
| 2022/0142697 A9 | 5/2022 | Toth et al. |
| 2022/0151674 A1 | 5/2022 | Sharma |

FOREIGN PATENT DOCUMENTS

| | | |
|---|---|---|
| CN | 101198288 A | 6/2008 |
| EP | 1236440 A1 | 9/2002 |
| EP | 1595507 A2 | 11/2005 |
| EP | 2349044 A1 | 8/2011 |
| EP | 2493407 A1 | 9/2012 |
| EP | 2981222 A1 | 2/2016 |
| JP | 2005501597 A | 1/2005 |
| WO | WO-0053112 A2 | 9/2000 |
| WO | WO-2005122938 A1 | 12/2005 |
| WO | WO-2006001455 A1 | 1/2006 |
| WO | WO-2008083407 A1 | 7/2008 |
| WO | WO-2010048007 A1 | 4/2010 |
| WO | WO-2011053599 A1 | 5/2011 |
| WO | WO-2011060301 A1 | 5/2011 |
| WO | WO-2014165715 A1 | 10/2014 |
| WO | WO-2017127760 A1 | 7/2017 |
| WO | WO-2017185097 A1 | 10/2017 |

OTHER PUBLICATIONS

Notice of Allowance dated Oct. 20, 2021 for U.S. Appl. No. 16/706,179.
Notice of Allowance dated Nov. 27, 2020 for U.S. Appl. No. 14/657,684.
Office action dated Jan. 29, 2021 for U.S. Appl. No. 15/880,958.
Office action dated May 6, 2021 for U.S. Appl. No. 16/247,404.
Allen-Bradley. AC Braking Basics. Rockwell Automation. Feb. 2001.4 pages. URL: http://literature.rockwellautomation.com/idc/groups/literature/documents/wp/drives-wp004_-en-p.pdf.
Allen-Bradley. What Is Regeneration? Braking / Regeneration Manual: Regeneration Overview. Revision 1.0. Rockwell Automation. Accessed Apr. 24, 2017. 6 pages. URL: https://www.ab.com/support/abdrives/documentation/techpapers/RegenOverview01.pdf.
Co-pending U.S. Appl. No. 16/706,179, filed Dec. 6, 2019.
Co-pending U.S. Appl. No. 16/819,386, filed Mar. 16, 2020.
European search report and opinion dated Nov. 18, 2016 for EP Application No. 14778196.7.
European search report and search opinion dated Apr. 16, 2013 for EP Application No. 09822443.
European search report and search opinion dated Jul. 10, 2013 for EP Application No. 10827399.
International search report and written opinion dated Feb. 2, 2011 for PCT/US2010/056591.
International Search Report and Written Opinion dated May 31, 2017 for International PCT Patent Application No. PCT/US2017/014456.
International Search Report and Written Opinion dated Jul. 7, 2017 for International PCT Patent Application No. PCT/US2017/029201.
International Search Report and Written Opinion dated Nov. 3, 2017 for International PCT Patent Application No. PCT/US2017/039326.
International search report and written opinion dated Dec. 10, 2009 for PCT/US2009/060703.
International search report and written opinion dated Dec. 14, 2010 for PCT/US2010/054150.
International Search Report dated Jul. 6, 2016 for PCT/US16/25509.
International Search Report dated Sep. 10, 2014 for PCT/US2014/032895.
Notice of allowance dated Jan. 9, 2014 for U.S. Appl. No. 13/938,032.
Notice of Allowance dated Jan. 27, 2017 for U.S. Appl. No. 13/236,471.
Notice of Allowance dated Jan. 27, 2017 for U.S. Appl. No. 14/508,856.
Notice of allowance dated Feb. 25, 2015 for U.S. Appl. No. 13/975,139.
Notice of allowance dated Mar. 5, 2012 for U.S. Appl. No. 13/281,846.
Notice of allowance dated Mar. 5, 2012 for U.S. Appl. No. 13/281,856.
Notice of allowance dated Mar. 29, 2013 for U.S. Appl. No. 12/605,546.
Notice of Allowance dated Apr. 24, 2018 for U.S. Appl. No. 15/410,723.

(56) References Cited

OTHER PUBLICATIONS

Notice of allowance dated May 9, 2014 for U.S. Appl. No. 12/944,466.
Notice of allowance dated May 24, 2013 for U.S. Appl. No. 12/605,929.
Notice of Allowance dated Aug. 2, 2016 for U.S. Appl. No. 13/281,805.
Notice of Allowance dated Aug. 6, 2019 for U.S. Appl. No. 15/008,341.
Notice of allowance dated Aug. 17, 2016 for U.S. Appl. No. 13/281,805.
Notice of allowance dated Sep. 10, 2019 for U.S. Appl. No. 15/488,270.
Notice of allowance dated Oct. 19, 2018 for U.S. Appl. No. 14/341,121.
Notice of allowance dated Nov. 15, 2012 for U.S. Appl. No. 12/541,043.
Notice of allowance dated Nov. 15, 2012 for U.S. Appl. No. 12/541,050.
Notice of allowance dated Nov. 15, 2018 for U.S. Appl. No. 14/341,121.
Notice of allowance dated Dec. 2, 2014 for U.S. Appl. No. 13/975,139.
Notice of Allowance dated Dec. 11, 2019 for U.S. Appl. No. 15/583,712.
Notice of allowance dated Dec. 14, 2017 for U.S. Appl. No. 13/857,068.
Office action dated Jan. 2, 2019 for U.S. Appl. No. 15/008,341.
Office action dated Jan. 28, 2013 for U.S. Appl. No. 12/605,546.
Office action dated Feb. 4, 2016 for U.S. Appl. No. 13/857,068.
Office action dated Feb. 19, 2019 for U.S. Appl. No. 15/488,270.
Office action dated Mar. 12, 2012 for U.S. Appl. No. 12/541,043.
Office action dated Mar. 12, 2012 for U.S. Appl. No. 12/541,050.
Office Action dated Mar. 14, 2017 for U.S. Appl. No. 15/410,723.
Office Action dated Mar. 31, 2016 for U.S. Appl. No. 13/281,805.
Office Action dated Apr. 5, 2017 for U.S. Appl. No. 13/857,068.
Office action dated Apr. 16, 2020 for U.S. Appl. No. 14/657,684.
Office Action dated Apr. 18, 2017 for U.S. Appl. No. 14/657,684.
Office Action dated Apr. 22, 2016 for U.S. Appl. No. 14/657,684.
Office action dated Apr. 24, 2014 for U.S. Appl. No. 13/975,139.
Office action dated May 2, 2019 for U.S. Appl. No. 14/657,684.
Office Action dated May 9, 2017 for U.S. Appl. No. 15/410,723.
Office action dated May 22, 2015 for U.S. Appl. No. 14/657,684.
Office action dated May 29, 2019 for U.S. Appl. No. 15/583,712.
Office action dated Jun. 5, 2015 for U.S. Appl. No. 13/857,068.
Office action dated Jun. 8, 2020 for U.S. Appl. No. 15/880,958.
Office action dated Jun. 15, 2018 for U.S. Appl. No. 14/864,379.
Office action dated Jun. 18, 2012 for U.S. Appl. No. 12/605,546.
Office action dated Jun. 28, 2018 for U.S. Appl. No. 14/341,121.
Office Action dated Jun. 29, 2016 for U.S. Appl. No. 14/508,856.
Office Action dated Jul. 5, 2016 for U.S. Appl. No. 13/236,471.
Office action dated Jul. 12, 2018 for U.S. Appl. No. 14/657,684.
Office action dated Jul. 23, 2015 for U.S. Appl. No. 13/281,805.
Office Action dated Sep. 7, 2016 for U.S. Appl. No. 13/857,068.
Office action dated Sep. 22, 2014 for U.S. Appl. No. 13/281,805.
Office action dated Sep. 24, 2015 for U.S. Appl. No. 13/236,471.
Office action dated Sep. 28, 2012 for U.S. Appl. No. 12/541,043.
Office action dated Sep. 28, 2012 for U.S. Appl. No. 12/541,050.
Office action dated Sep. 28, 2012 for U.S. Appl. No. 12/605,929.
Office action dated Oct. 9, 2014 for U.S. Appl. No. 13/857,068.
Office action dated Oct. 24, 2014 for U.S. Appl. No. 13/975,139.
Office action dated Nov. 1, 2018 for U.S. Appl. No. 15/583,712.
Office Action dated Nov. 2, 2016 for U.S. Appl. No. 14/657,684.
Office action dated Nov. 6, 2013 for U.S. Appl. No. 13/938,032.
Office action dated Nov. 27, 2017 for U.S. Appl. No. 14/341,121.
Office action dated Dec. 4, 2014 for U.S. Appl. No. 13/236,471.
Office action dated Dec. 5, 2017 for U.S. Appl. No. 14/864,379.
Office action dated Dec. 6, 2011 for U.S. Appl. No. 13/281,846.
Office action dated Dec. 16, 2014 for U.S. Appl. No. 13/281,805.
Office action dated Dec. 22, 2011 for U.S. Appl. No. 13/281,856.
Notice of Allowance dated Jan. 26, 2022 for U.S. Appl. No. 16/706,179.
Office action dated Jan. 25, 2022 for U.S. Appl. No. 16/222,757.
Office action dated Apr. 28, 2022 for U.S. Appl. No. 16/435,323.
Office action dated May 2, 2022 for U.S. Appl. No. 16/247,404.
Office Action dated Jun. 10, 2022 for U.S. Appl. No. 16/819,386.
Office action dated Jul. 25, 2022 for U.S. Appl. No. 16/222,757.

* cited by examiner

FLUID MANAGEMENT SYSTEM

CROSS-REFERENCE TO RELATED APPLICATION

This application claims the benefit of provisional application No. 62/866,876, filed on Jun. 26, 2019, the full disclosure of which is incorporated herein by reference.

BACKGROUND OF THE INVENTION

The present invention relates generally to a surgical fluid management system and more particularly to a surgical fluid management system of the type used in endoscopic procedures.

Surgical fluid management systems typically deliver a fluid, such as saline, to a targeted working space or body cavity to provide access and visibility to the physician performing a procedure in the working space or body cavity. The fluid usually provides a pressure sufficient to "open" the space (i.e. create a working space for the procedure) as well as flushing blood and debris from the space. Typically, the surgical fluid management system includes a fluid bag as a source of fluid and a control system including a pump for delivering the fluid from the fluid bag to a surgical working space a preset fluid pressure.

Surgical fluid management systems are often inconvenient to use and difficult to monitor. Further, the control systems of such fluid management systems are often unable to accurately measure pressure in a working space when the patient and the fluid management console are at different elevations.

One challenge with present fluid management systems is the early detection of empty fluid bags. While fluid bags are usually changed at regular intervals and/or when observed to be low on fluid, such "manual" protocols are subject to human error.

It would therefore be beneficial to provide improved surgical fluid management systems that overcome at least some of these shortcomings. In particular, it would be desirable to provide surgical fluid management systems with an ability to monitor when the fluid in a bag has been exhausted. At least some of these objectives will be met by the inventions described below.

Listing of Background Art

US2016/0242844; US2018/0326144; US2019/0030235; and US2020/0030527, have common inventorship and describe surgical fluid management systems. US2020/0030527 describes a pressure-transmitting membrane located in a wall of a cassette housing in fluid communication with a fluid delivery lumen. FIGS. 1-5 of the present application are included in US2020/0030527. The full disclosure of US2020/0030527 is incorporated herein by reference.

SUMMARY OF THE INVENTION

In general, the fluid management system of the present invention include a disposable cassette carrying inflow and/or outflow tubing sections that are configured for releasably mating with a control unit and roller pump head(s). The fluid management systems can be adapted to automatically recognize the type of disposable cassette and the volume of fluid in an inflow source. During operation, the system can calculate pressure in the working space based on fluid pressure in the cassette tubing set, and provide for inflow and outflow control to maintain a desired pressure in the working space or adjust other operating parameters. Other features, objects, and advantages will be apparent from the description and drawings, and from the claims.

The present invention provides improved fluid management systems and methods for their use. In particular, the present invention provides a disposable tubing cassette, a console for detachably receiving the disposable tubing cassette, and methods for mounting and replacing the tubing cassette on the console. The disposable tubing cassette will usually include a first flexible tubing loop, where the tube is used for delivering fluid from a fluid source to a patient. A second tube may be used for removing fluid from the patient and delivering the fluid to a disposal receptacle. The fluid management systems may also be configured to alert the user when the cassette has been successfully loaded or, conversely, when the cassette has not been successfully loaded. Further capabilities include sensing conditions of the fluid, in particular, positive and negative pressures in a fluid in an inflow pathway of the cassette. Automatic locking capabilities may also be provided by a motor and control mechanism carried by the console.

In a first specific aspect of the present invention, a surgical fluid management system comprises a pump configured to deliver fluid to a patient from a replaceable fluid bag. A controller is operatively connected to the pump, and a sensor is operatively connected to the pump and configured to measure a fluid flow or pump parameter associated with the presence of fluid in the replaceable fluid bag. The controller is programmed or configured to detect when the fluid flow or pump parameter indicates that the replaceable fluid bag is empty or near empty.

In specific instances or examples of the present invention, the sensor measures a fluid flow parameter selected from pressure and flow rate. In alternative instances or examples of the present invention, the sensor measures a pump parameter selected from operating voltage, current consumption, and pump speed. In all cases, the sensor measures the parameter in a manner where a change in the measured parameter correlates with the availability of fluid in the replaceable and indicates when fluid bag is empty or near empty.

In further specific instances or examples of the present invention, the pump comprises a rotor with a peristaltic output producing compression pressure peaks and decompression pressure troughs. The sensor comprises a pressure sensor, and the fluid flow parameter comprises a difference between the compression pressure peak and the decompression pressure trough. A difference between the compression pressure peak and the decompression pressure trough which falls below a minimum threshold value indicates that the replaceable fluid bag is empty or near empty.

In other specific instances or examples of the present invention, the difference between the compression pressure peak and the decompression pressure trough begins to fall when fluid delivered by pump is mixed with air as occurs when the replaceable fluid bag empties.

In still more specific instances or examples of the present invention, the pump comprises a pressure-sensing membrane configured to interface with a cassette carrying flexible tubing and wherein the cassette comprises a pressure-transmitting membrane in the cassette housing in fluid communication with a lumen in the flexible tubing, and wherein the pressure sensor is configured to measure fluid pressure in the flexible tubing.

In another aspect of the present invention, a method for managing fluids during a medical procedure comprises attaching a replaceable fluid bag to a pump. The pump is operated to pump fluid from the replaceable fluid bag to a patient, and a fluid flow or pump parameter associated with the presence of fluid in the replaceable fluid bag is sensed. The fluid flow or pump parameter is monitored to determine when the parameter indicates that the replaceable fluid bag is empty or near empty.

The methods of the present invention may further comprise any one or more of alerting a user when the replaceable fluid bag is detected to be empty or near empty, automatically stopping the pump when the replaceable fluid bag is detected to be empty or near empty, and replacing the replaceable fluid bag when the replaceable fluid bag is detected to be empty or near empty.

In specific instances or examples of the methods of present invention, a fluid flow or pump parameter is sensed, typically comprising measuring a fluid flow parameter selected from pressure and flow rate. In alternative instances or examples of the methods of present invention, a fluid flow or pump parameter is sensed, typically comprising measuring a pump parameter selected from operating voltage, current consumption, and pump speed.

In an exemplary instance of the methods herein, the pump comprises a rotor with a peristaltic output producing compression pressure peaks and decompression pressure troughs. The sensor measures a pressure output of the pump, and the fluid flow parameter comprises a difference between a measured compression pressure peak from the pump and a measured decompression pressure trough from the pump. Detecting comprises detecting when a difference between the measured compression pressure peak and the measured decompression pressure trough falls below a minimum threshold value indicating that the replaceable fluid bag is empty or near empty.

DETAILED DESCRIPTION OF THE INVENTION

Figure 1:
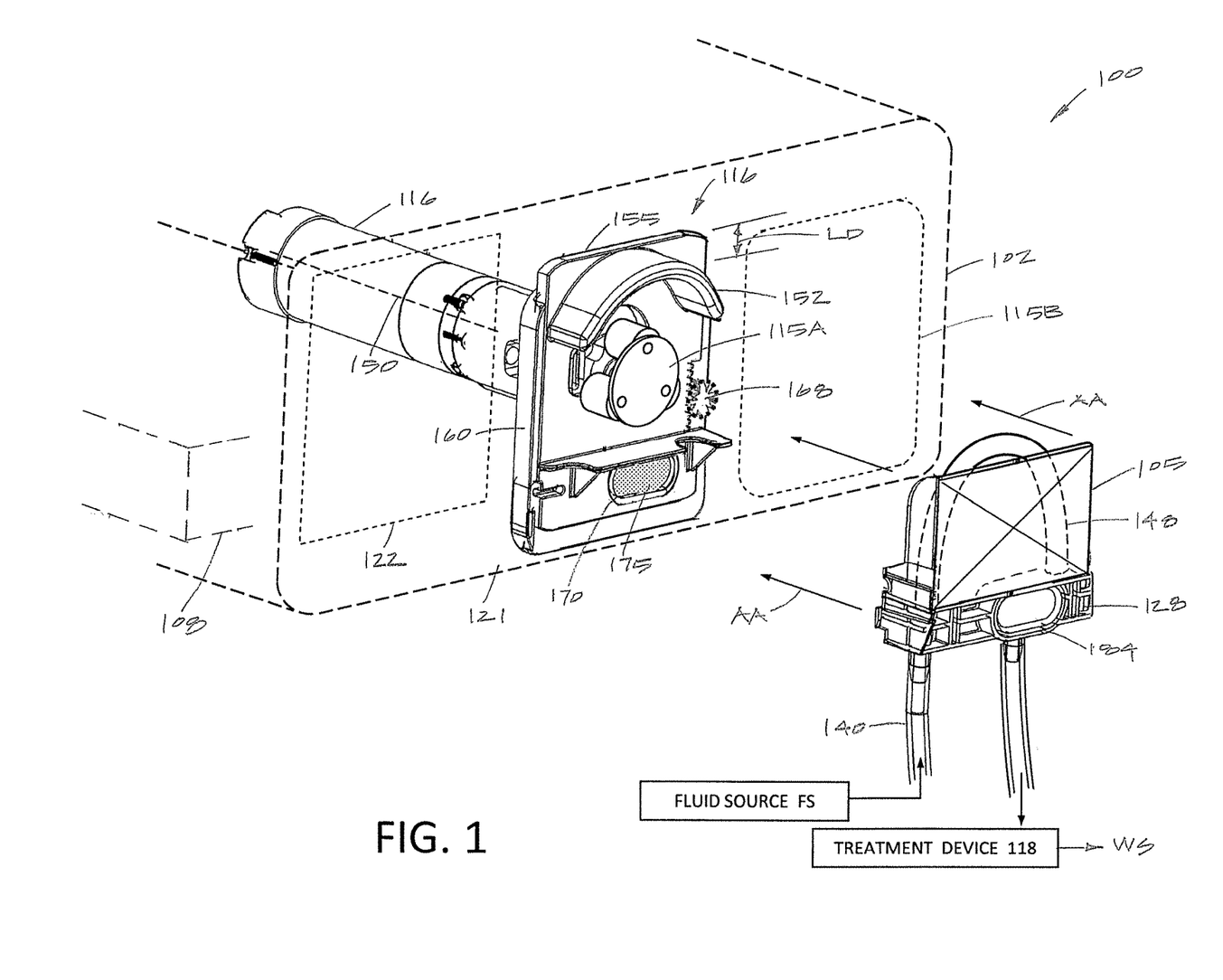
FIG. 1 is a perspective view of a console or control unit of a fluid management system in partly phantom view that includes an inflow peristaltic pump and a detachable cassette that carries an inflow tubing loop adapted for engaging the peristaltic pump head or rotor, further showing a fixed base plate that carries the pump motor and rotor together with a sliding base plate to which the cassette is attached.

FIG. 1 illustrates a fluid management system 100 of the invention which includes a console or control unit 102 and a disposable tubing cassette 105 (FIGS. 1-2) that carries a single loop of an inflow tubing set for coupling to an inflow pump 115A further described below. The fluid management system 100 is used in endoscopic procedures, which can be a urology procedure, a gynecology procedure or an arthroscopic surgery, to provide inflows and outflows of a pressurized fluid to a working space or body cavity. The fluid can be delivered to provide and maintain a pre-set pressure level within the working space. The fluid pressure in the space is controlled by a controller 108 and control algorithms therein carried by the control unit 102 which can calculate the fluid pressure in the working space based on sensed pressure in a fluid inflow path at the control unit 102 and then vary the inflow and/or outflow to maintain a targeted pressure or a targeted pressure in combination with an inflow or outflow rate. An outflow pump mechanism is not shown in detail, which could be a second pump 115B (phantom view) in the control unit 102 or wall suction could be used.

Figure 2:
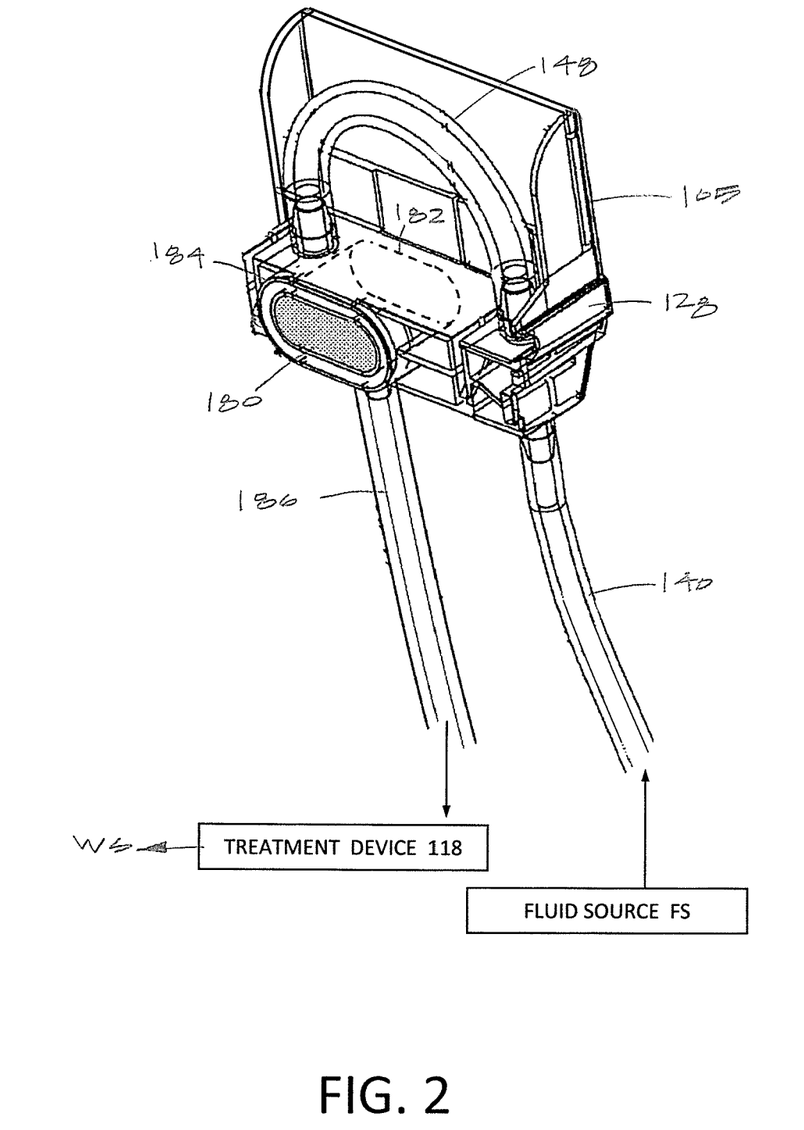
FIG. 2 illustrates a back side of the cassette of FIG. 1 further showing a flexible membrane of a sensing window in the fluid inflow path of the cassette adapted to interface with a pressure sensor membrane on the console of FIG. 1.

Referring to FIGS. 1-2, the console or control unit 102 carries a first peristaltic pump 112 comprising pump head 115A with rollers and a motor 116 (see FIG. 1) wherein the pump provides inflows from a fluid source FS into a working space WS. Typically, the fluid inflows and outflows are provided through one or more channels in an endoscope and/or a treatment device 118. The control unit 102 includes a microprocessor or controller 108 for controlling the inflow pump and may further include an RF generator or other energy source for coupling to a treatment device 118 and/or a power source to powering a motor in the treatment device 118.

In FIG. 1, one variation of control unit 102 has a front surface 121 which can include a touch screen (not shown) that permits the operator to control system operations. For example, the touch screen 122 can allow the operator select a target pressure, flow rate and/or mode of operation. In one variation described further below, the touch screen 122 can indicate when the user positions the cassette 105 in the correct interface with the control unit 102, and thereafter the control unit can automatically activate a locking motor to engage and move the cassette 105 from a pre-locked position to a locked position to engage the pump heads as will be described below. In these steps, the touch screen 122 can display the pre-locked and locked positions. The touch screen 122 can then be touched to actuate the locking motor to unlock the cassette 105 following a procedure. In other variations, the cassette 105 can be manually inserted and pushed into a locked positioned. It has been found that significant manual force may be required to push the cassette 105 into a locked position, and the amount of force may vary depending on the orientation of the rollers in the pump heads 115A and 115B, and for this reason a motorized locking system may be preferred.

Referring to FIGS. 1-2, the cassette 105 includes a plastic molded housing or body 128 that carries a portion of a tubing set, and more particularly a flexible loop of inflow tubing 140. The tubing is typically a flexible polymer material having a diameter ranging between about ¼" to ½" and is adapted to cooperate with the first pump head 115A (see FIG. 1). The tubing loop portion 148 in the cassette 105 (see FIGS. 1-2) extends in a semicircular arc of at least 90° or at least 120° in the plane of the cassette, where the plane of the cassette is adapted to align with the first pump head 115A. As shown in FIG. 2, the plane of the tubing loop portion is perpendicular to the axis 150 of a shaft of the pump motor 116 and the pump head 115A.

Referring to FIG. 1, it can be seen as the tubing loop portion 148 within the cassette 105 is adapted to be inserted between the pump head 115A (rotor or roller assembly) and the arcuate structure or eyebrow 152 that interfaces with the tubing loop 148 and pump head 115A.

From FIG. 1, it can be understood how the cassette 105 is coupled with the control unit 102. The cassette 105 is initially pushed inward toward the front panel 121 of the control unit 102 as indicated by arrows AA. The tubing loop portion 148 of the inflow tubing is then loosely positioned in the space between eyebrow 152 and the pump head 115A.

It can be understood that after inserting the cassette 105 and tubing loop over the pump head 115A, it is necessary to compress the tubing loop portion 148 between the pump head 115A and the eyebrow 152 which is be accomplished by the downwards sliding movement of the sliding base plate 155 which carries eyebrow 152 and the cassette 105. The pump head 115A and motor 116 are attached to the fixed base plate 160 which is coupled to the front panel 121 of the control unit 102 (FIG. 1). As can be understood from FIG. 1, the sliding base plate 155 and eyebrow 152 together with the cassette 105 can be moved downward a locking distance indicated at LD which thus compresses the tubing loop portion 148 between the eyebrow 152 and the pump head 115A.

A locking motor (not visible) with a gear reduction mechanism rotates a gear 168 that is adapted to move the sliding base plate 155 the locking distance LD to thereby move the cassette 105 from a pre-locked position to a locked position. The locking motor can be activated by microswitch (not shown) in the console 102 or sliding base plate 155 that is activated when the cassette 105 is pushed inwardly against the sliding base plate 155.

Still referring to FIG. 1, it can be seen that the sliding base plate 155 carries a pressure sensor 170 with a pressure-sensing or sensor membrane 175 that is adapted to contact a flexible pressure-transmitting membrane 180 carried by the cassette 105 (see FIG. 2). In FIG. 2, it can be seen that the cassette membrane 180 is disposed on a side of a fluid chamber 182 in the cassette that communicates with fluid inflows or static fluid in the inflow tubing 140. As can be understood from FIG. 2, the flow path in the inflow tubing 140 extends through a housing 184 that carries the fluid chamber 182 and the cassette membrane 180 is adapted to flex inwardly and outwardly depending on pressure of the fluid in the chamber 182 and the lumen 186 of the inflow tubing 140. Thus, the flexible membrane 180 carried by the cassette 105 interfaces with the pressure sensor membrane 175 carried by the sliding base plate 155. Some similar pressure sensing mechanisms are known in the prior art. However, in this variation, the interface of the cassette membrane 180 and pressure sensor membrane 175 differ in that the membranes 175 and 180 are aligned in direct opposition to one another after the cassette 105 is pushed onto the pump head 115A and thereafter the membranes 175 and 180 remain in a non-sliding or fixed relationship as the sliding base plate 155 is moved to compress the tubing loop 148 against the pump head 115A.

By measuring fluid pressure with such a sensor mechanism in the control unit 102, the fluid pressure in the working space can be calculated, which is known in the prior art. Of particular interest in the present invention, the pressure sensing mechanism corresponding to the invention is configured to allow the pressure sensor 170 carried by the sliding base plate 155 to sense positive pressure in the fluid inflows as well as negative pressure. Prior art systems were designed only for sensing positive pressure in a fluid inflow.

In some surgical procedures such as gynecology, it is important to regulate or maintain "actual" fluid pressure in a working space WS within a narrow predetermined range or a not-to-exceed pressure. Further, it can be understood that the elevation of pump head 115A relative to the patient and the working space WS can make the fluid pressure in a working space different from the measured pressure in the cassette 105. In other words, the "actual" fluid pressure in a working space WS will differ from the pressure sensed at the control unit 102 simply based on the elevation difference between the control unit 102 and the working space WS. For example, in a gynecology procedure, the variance in the height of the control unit 102 relative to the working space WS can result in a sensed pressure at the control unit 102 that varies by up to 10% or more from the actual pressure in the working space WS. Over the time of a surgical procedure, such an inaccurate pressure measurement can be problematic and potentially cause injury to the patient by an overpressure in the working space WS.

Thus, in a typical procedure, after the patient is prepared for surgery and the working space WS is filled with fluid and the tubing sets have been purged of air, a difference in elevation of the treatment device 118 or working space WS relative to the console 102 can be calculated by a positive or negative pressure reading the pressure sensor 170 which interfaces with the cassette membrane 180.

In order for the sensor membrane 180 to measure negative pressures, or flex inwardly relative to the cassette, a mechanism is provided to detachably adhere the cassette membrane 180 to the sensor membrane 175. Now referring to FIG. 3A, in one variation, the sensor membrane 175 and the cassette membrane 180 each carried a magnet 185a, 185b (or a magnetic responsive material in one membrane that is attracted to a magnet in the other membrane). Thus, in FIG. 3B, it can be seen that a positive pressure in the fluid 188 against the cassette membrane 180 flexes the sensor membrane 175 and the increased pressure in fluid 190 in the sensor is read by the sensing elements 192. In FIG. 3C, it can be seen that if is negative pressure in the fluid 188 in the cassette inflow path, then the cassette membrane 180 will flex inwardly relative to the cassette wherein such a negative pressure influences the sensor membrane 175 which again can sensed by the sensing elements 192. Prior to the procedure, the sensing elements 192 can be zeroed-out to have a baseline value, and thereafter the elevation of the treatment device 118 and the working space WS relative to the console 102 can be determined by positive pressure as illustrated in FIG. 3B or by negative pressure as illustrated in FIG. 3C.

Figure 3A:
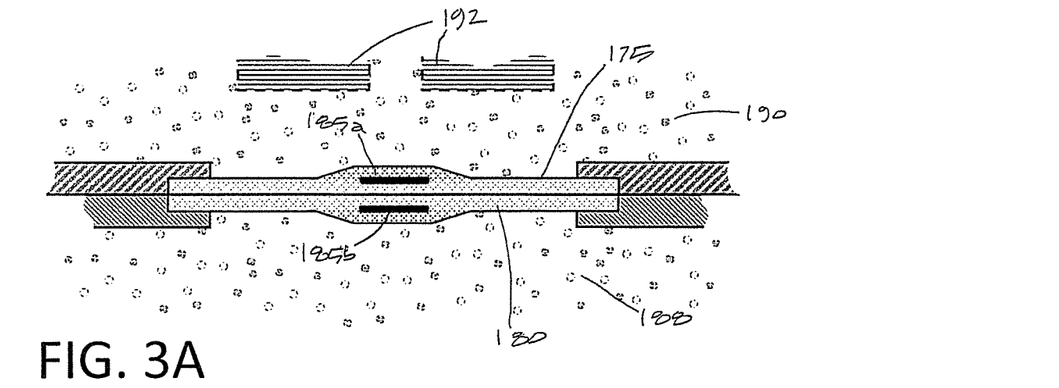
FIG. 3A is an enlarged schematic view of the flexible cassette membrane interfacing with a sensor membrane of a pressure sensor carried by the console in a first static condition, wherein both membranes carry magnets for detachable coupling of the membranes.
Figure 3B:
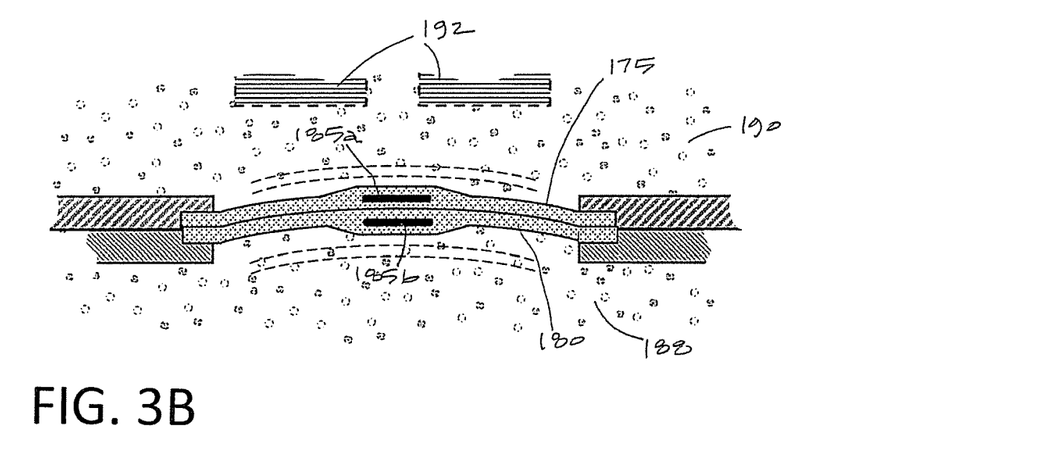
FIG. 3B is a schematic view of the membranes of FIG. 3A showing the flexible cassette membrane flexing outwardly relative to the cassette in response to positive fluid pressure in the fluid inflow path which flexes the sensor membrane and allows the sensor elements to calculate the positive pressure.
Figure 3C:
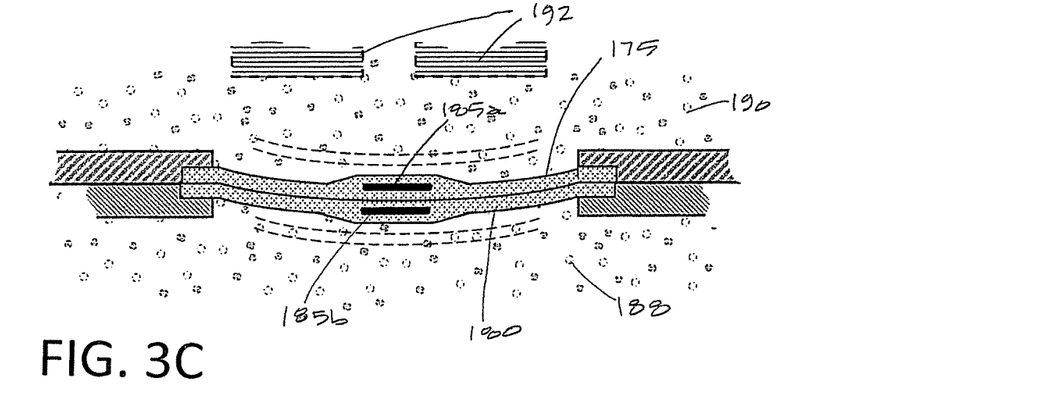
FIG. 3C is a view of the membranes of FIG. 3B showing the flexible cassette membrane flexing inwardly relative to the cassette in response to negative fluid pressure in the fluid inflow path which flexes the sensor membrane and allows the sensor elements to calculate the negative pressure.

FIG. 3A-3C show a first magnet 185*a* in the sensor membrane 175 and a second magnet 185*b* in the cassette membrane 180, but it should be appreciated that a single magnet in one membrane and magnetic responsive material such as iron powder can be dispersed in the second membrane to insure that the membranes 175, 180 remain coupled to one another whether there is positive or negative pressure in the fluid 188 in the inflow path in the cassette 105.

Figure 4:
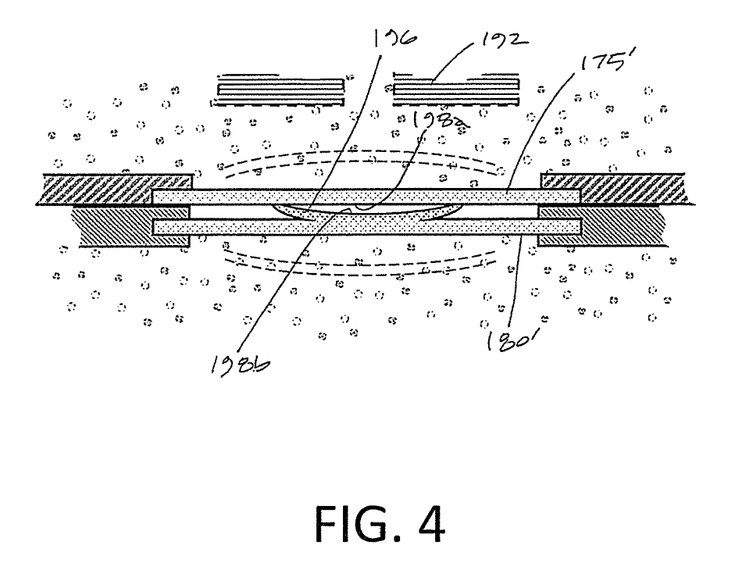
FIG. 4 is an enlarged view of another variation of a flexible cassette membrane that interfaces with a sensor membrane, wherein the cassette membrane carries at least one suction cup element for detachable coupling of the cassette and sensor membranes.

FIG. 4 illustrates another variation which couples the sensor membrane 175' with the cassette membrane 180' which comprises at least one flexible suction cup element 196 that detachably couples together the exterior surfaces one 198*a* and 198*b* of the two membranes 175' and 180'. It should be appreciated that other mechanisms are possible for detachably coupling the membranes, such as providing one membrane surface with microfabricated synthetic setae of the type developed to mimic setae on gecko's feet. As is well known, gecko setae are adapted to detachably contact and adhere to smooth surfaces. In another variation, the surface of the cassette membrane 180 may be covered with removable protective element, and the membrane surface can be provided with a slightly tacky adhesive similar to a Post-It in order to allow for detachably coupling of the two membranes 175, 180. In another variation, the cassette membrane may be covered by a removable protective element and the membrane surface can carry a viscous fluid or grease that is sufficient to maintain adherence between the two membranes during use.

Figure 5A:
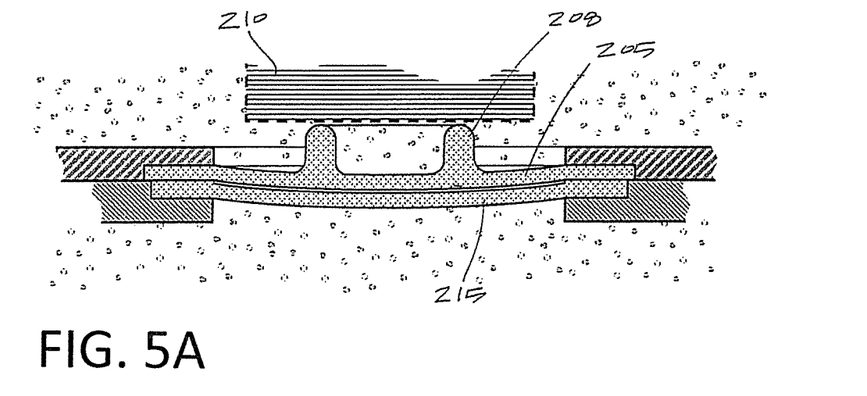
FIG. 5A is an enlarged schematic view of another variation of flexible cassette membrane that interfaces with a sensor membrane that has a projecting feature that contacts a pressure or force sensor in a first static condition.
Figure 5B:
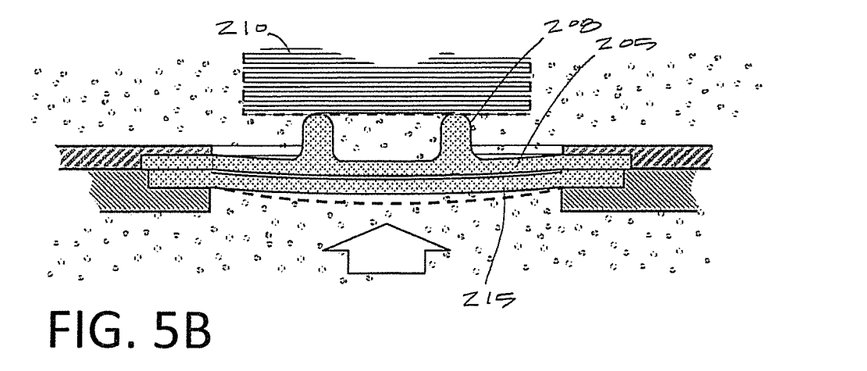
FIG. 5B is a view of the sensor membrane of FIG. 5A showing the flexible cassette membrane flexing outwardly relative to the cassette in response to positive fluid pressure in the fluid inflow which flexes the sensor membrane and the projecting feature or element into the force sensor allowing calculation of the positive pressure.
Figure 5C:
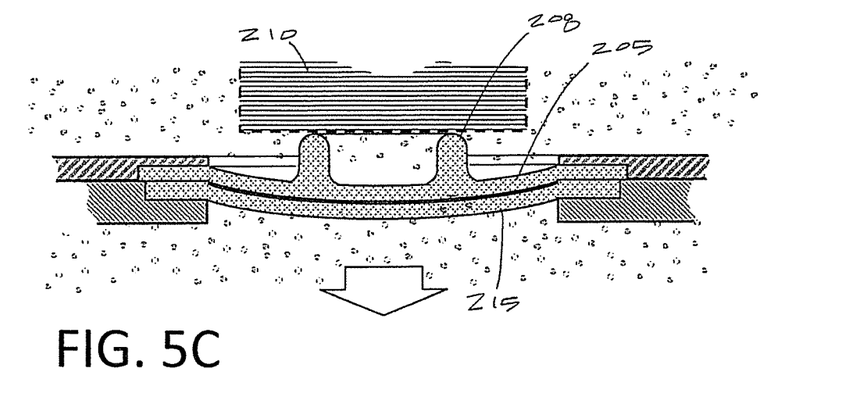
FIG. 5C is a view of the sensor membrane of FIG. 5A showing the flexible cassette membrane flexing inwardly relative to the cassette in response to negative fluid pressure which flexes the sensor membrane and the projecting feature or element away from the force sensor allowing calculation of the negative pressure.

Now turning to FIG. 5A-5C, another variation of sensing mechanism is shown wherein the sensor membrane 205 includes a projecting feature or element 208 that contacts a force sensor element 210 and wherein in a repose position, the sensor membrane 205 is flexed outwardly. Thereafter, following the locking of the cassette 105 and the sliding base plate 155 as described previously, the cassette membrane 215 will be flexed inwardly (relative to the cassette 105) in response to the outward bulging of the sensor membrane 205. Thus in FIG. 5B, it can be seen that positive pressures in the flow path and cassette can cause both membranes 205, 215 to flex in the direction of the force sensing element 210 and wherein the force sensor can determine the positive pressure. Referring to FIG. 5C, the opposite is also possible where a negative pressure in the fluid in the inflow path results in the membrane sensor membrane 205 flexing outwardly relative to the console 102 which then can be read by the force sensing element 210 to calculate the negative pressure.

The console 102 carries a controller 108 with a microprocessor that operates in accordance with algorithms to control inflows and outflows of a fluid to a working space to maintain a pre-set pressure level within the space. The console 102 can further include an RF generator or other energy source for coupling to a surgical instrument. The system optionally can monitor pressure in a space directly with a pressure sensor in a fluid communication with the space through an open channel in a device which then will allow the controller 108 to vary inflows and/or outflows to maintain the targeted pressure.

Figure 6:
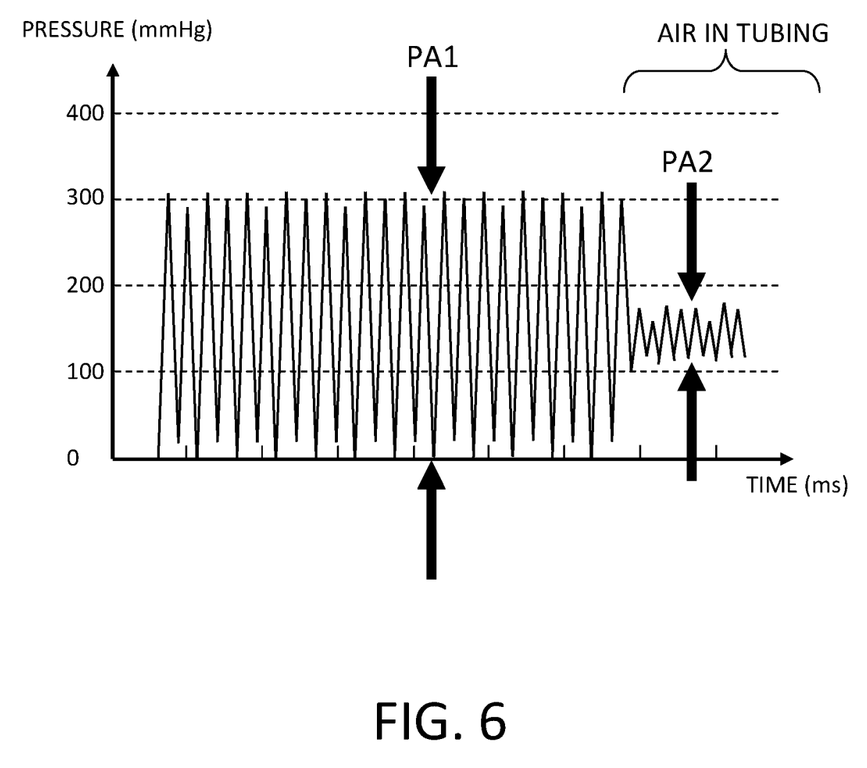
FIG. 6 is a chart showing the amplitude of pressure waves in inflow tubing which can be sensed by the pressure sensing mechanisms described above to detect air in the tubing which indicates an empty saline bag or fluid source.

In another aspect of the invention, the controller 108 is adapted to sense when the fluid source FS is empty. As described above, typically the fluid source FS comprises a bag of saline solution which is coupled to the inflow tubing 140 including tubing loop 148 with lumen 186 therein (see FIG. 2) which extends through the cassette 105 and to the treatment device 118 or the treatment site. It can be understood that the three rollers of the pump head 115A (see FIG. 1) will create large pressure waves in saline in the lumen 186 of the inflow tubing 140 during use. In one variation of a fluid management system, the pressure waves will have a peak pressure (referred to as a "compression pressure peak" in the claims) between about 200 mmHg to 300 mmHg during compression of the tubing as each roller engages and disengages the tubing loop 148 in the cassette 105 to thereby pump saline to the treatment device or site (see FIG. 6). When the roller decompresses the tubing 140, the pressure drops to zero or close to zero (referred to as a "compression pressure trough" in the claims). In FIG. 6, a typical pressure wave amplitude is indicated at PA1. It can be understood that when the fluid source FS or saline bag is empty or close to empty, air from the interior of the saline bag will enter the lumen 186 of the inflow tubing 140 which communicates with the pressure transmitting membrane 180 in the cassette 105 which is sensed by the pressure receiving membrane 175 in the console 103. When the lumen 186 of the inflow tubing 140 is filled with fluid, it can be understood that the amplitude of the pressure waves (peak to peak pressure difference) will be consistent except it may vary depending on the selected inflow rate which corresponds to pump speed or RPM.

When the saline bag comprising the fluid source is empty, the pump head 115A will start to pump a combination of air and saline into the tubing 140. In this situation, the peak pressures shown in FIG. 6 will be altered (lowered relative to the compression pressure peak before the bag was near empty) significantly since the combination of air and saline in the lumen 186 is compressible as the rollers of the pump head 115A compressed and decompress the tubing 140.

As can be understood from the disclosure above, the pressure sensing mechanism consisting of the membranes 175 and 180 will continuously monitor the pressure peaks and valley to determine treatment site pressure by averaging the pressures over a short time interval. In another variation of the invention, the same pressure sensing mechanisms can be used in a detection algorithm to detect an empty saline bag. In one variation of detection algorithm, the typical pressure amplitudes can be stored in a look-up library in the controller 108 for different selected fluid inflow rates. Alternatively, using machine learning, the control system may determine the expected compression pressure peaks and decompression pressure troughs as a function of fluid flow and/or other operational parameters during use and/or over time. Still further alternatively, the control system can be configured to measure the differential pressure amplitude at the start of a fluid delivery procedure and/or whenever a fluid bag is replaced to establish a baseline for that delivery (measured pressure may vary due tubing configurations, bag placement, etc.), where a subsequent drop below the initial differential pressure amplitude indicates that the bag is empty or near empty.

During use, the detection algorithm can sense the maximum and minimum pressures for each engagement of the rollers with the tubing 140 to determine the amplitude (peak to peak) of pressure waves. Then, the algorithm can continuously sample such amplitudes over a time interval, for example, from 0.5 second to 5 seconds. Referring to FIG. 6, a pressure wave amplitude indicated at PA2 is lower than a threshold amplitude for a given flow rate which will indicate that there is air in the system and an empty saline bag. The controller 108 then can provide a signal to alert the operator that the saline bag is empty and/or can automatically turn off the pump.

In another variation, the amplitude of the pressure waves can be factored by or inferred from a motor parameter such as RPM, voltage, current load, or the like, to provide an operating parameter for comparison to a threshold parameter that indicates air in tubing 140. Normal and "bag empty" operational ranges for any one or combination of such parameters can be pre-determined and stored in a look-up table and/or determined by machine learning algorithms as with the pressure determinations described above. By this means, the fluid management system 100 can reliably detect an empty saline bag with a controller algorithm and no additional hardware.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A surgical fluid management system comprising:
    a pump configured to deliver fluid to a patient from a replaceable fluid bag;
    a controller operatively connected to the pump; and
    a pressure sensor operatively connected to the pump and configured to measure a fluid pressure parameter associated with the presence of fluid in the replaceable fluid bag;
    wherein the controller is programmed or configured to detect when the fluid pressure parameter indicates that the replaceable fluid bag is empty or near empty; and
    wherein the pump comprises a rotor with a peristaltic output producing compression pressure peaks and decompression pressure troughs, wherein the fluid pressure parameter comprises a difference between a measured compression pressure peak and a measured decompression pressure trough, and wherein the controller is configured to indicate that the replaceable fluid bag is empty or near empty when the difference between the measured compression pressure peak and the measured decompression pressure trough falls below a minimum threshold value.

2. The surgical fluid management system of claim 1, wherein the pump comprises a pressure-sensing membrane configured to interface with a cassette including a cassette housing carrying a flexible tubing and wherein the cassette comprises a pressure-transmitting membrane in the cassette housing in fluid communication with a lumen in the flexible tubing, and wherein the pressure sensor is configured to measure fluid pressure in the flexible tubing.

3. A method for managing fluids during a medical procedure, said method comprising:
    attaching a replaceable fluid bag to a pump, wherein the pump comprises a rotor with a peristaltic output producing compression pressure peaks and decompression pressure troughs;
    operating the pump to pump fluid from the replaceable fluid bag to a patient;
    sensing a pressure parameter associated with the presence of fluid in the replaceable fluid bag, wherein the sensed pressure parameter comprises a difference between a measured compression pressure peak from the pump and a measured decompression pressure trough from the pump; and
    detecting when the difference between the measured compression pressure peak and the measured decompression pressure trough falls below a minimum threshold value indicating that the replaceable fluid bag is empty or near empty.

4. The method of managing fluids as in claim 3, further comprising alerting a user when the replaceable fluid bag is detected to be empty or near empty.

5. The method of managing fluids as in claim 3, further comprising automatically stopping the pump when the replaceable fluid bag is detected to be empty or near empty.

6. The method of managing fluids as in claim 3, further comprising replacing the replaceable fluid bag when the replaceable fluid bag is detected to be empty or near empty.

* * * * *